US009617606B2

(12) United States Patent
Mizutani et al.

(10) Patent No.: US 9,617,606 B2
(45) Date of Patent: Apr. 11, 2017

(54) OLIGONUCLEOTIDE FOR HIV DETECTION, HIV DETECTION KIT, AND HIV DETECTION METHOD (71) Applicant: Japan Science and Technology Agency, Kawaguchi-shi, Saitama (JP)

(72) Inventors: Taketoshi Mizutani, Shinagawa-ku (JP); Aya Ishizaka, Shinagawa-ku (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 14/374,116

(22) PCT Filed: Jan. 24, 2013

(86) PCT No.: PCT/JP2013/051389
§ 371 (c)(1),
(2) Date: Jul. 23, 2014

(87) PCT Pub. No.: WO2013/111800
PCT Pub. Date: Aug. 1, 2013

(65) Prior Publication Data
US 2014/0370496 A1 Dec. 18, 2014

(30) Foreign Application Priority Data

Jan. 25, 2012 (JP) ................................ 2012-013087

(51) Int. Cl.
*C12Q 1/68* (2006.01)
*C12Q 1/70* (2006.01)
(52) U.S. Cl.
CPC .......... *C12Q 1/703* (2013.01); *C12Q 1/6855* (2013.01); *C12Q 2600/158* (2013.01)
(58) Field of Classification Search
None
See application file for complete search history.

(56) References Cited

U.S. PATENT DOCUMENTS

| 5,030,714 | A | * | 7/1991 | Alizon et al. ................. 530/326 |
| 5,837,464 | A | * | 11/1998 | Capon et al. ..................... 435/5 |
| 5,874,564 | A | * | 2/1999 | Ecker et al. ................ 536/24.5 |
| 6,025,124 | A | | 2/2000 | Adams et al. |
| 2006/0172325 | A1 | * | 8/2006 | Brownstein et al. ............. 435/6 |
| 2008/0182239 | A1 | * | 7/2008 | Mullinax et al. ................. 435/6 |
| 2011/0046982 | A1 | * | 2/2011 | Arya et al. ........................ 705/3 |
| 2011/0124050 | A1 | | 5/2011 | Engel et al. |

FOREIGN PATENT DOCUMENTS

| CN | 1271020 | A | 10/2000 |
| CN | 101970693 | A | 2/2011 |
| CN | 101978072 | A | 2/2011 |
| JP | 2007295896 | A | 11/2007 |
| JP | 2010535525 | A | 11/2010 |
| WO | 199117246 | | 11/1991 |
| WO | WO 2004041194 | A2 * | 5/2004 |
| WO | 2004048511 | A2 | 6/2004 |
| WO | WO 2009128960 | A2 * | 10/2009 |
| WO | WO 2010099169 | A2 * | 9/2010 |

OTHER PUBLICATIONS

Mahajan et al. (Nanotherapeutics Using an HIV-1 Poly A and Transactivator of the HIV-1 LTR-(TAR-) Specific siRNA, Patholog Res Int. 2011;2011:719139. doi: 10.4061/2011/719139. Epub May 10, 2011).*
Levine et al. (Gene transfer in humans using a conditionally replicating lentiviral vector, Published online before print Nov. 7, 2006, doi: 10.1073/pnas.0608138103 PNAS Nov. 14, 2006 vol. 103 No. 46 17372-17377).*
Weiner et al. (Kits and their unique role in molecular biology: a brief retrospective, BioTechniques 44:701-704 (25th Anniversary Issue, Apr. 2008)).*
Stratagene (Gene Characterization Kits; 1988).*
Merriam-Webster definition of represent, attached, accessed Jan. 22, 2015, available at http://www.merriam-webster.com/dictionary/represent.*
Bennasser et al. (HIV-1 TAR RNA Subverts RNA Interference in Transfected Cells through Sequestration of TAR RNA-binding Protein, TRBP, J Biol Chem. Sep 22, 2006;281(38):27674-8. Epub Aug. 3, 2006).*
Shi et al. (Facile means for quantifying microRNA expression by real-time PCR, Biotechniques. Oct. 2005;39(4):519-25).*
Yeung et al., Pyrosequencing of small non-coding RNAs in HIV-1 infected cells: evidence for the processing of a viral-cellular double-stranded RNA hybrid, Nucleic Acids Res. Oct. 2009; 37(19): 6575-6586. Published online Sep. 3, 2009.*
Mizutani et al. "Loss of the Brm-Type SWI/SNF Chromatin Remodeling Complex is a Strong Barrier to the Tat-Independent Transcriptional Elongation of Human Immunodeficiency Virus Type 1 Transcripts." Journal of Virology (2009) 11569-11580.
Emiliani et al. "Mutations in the tat Gene are Responsible for Human Immunodeficiency Virus Type 1 Postintegration Latency in the U1 Cell Line." Journal of Virology (1998) 1666-1670.
Adams et al. "Cellular Latency in Human Immunodeficiency Virus-Infected Individuals with High CD4 Levels can be Detected by the Presence of Promoter-Proximal Transcripts." Proc. Natl. Acad. Sci. (1994) 91:3862-3866.
Communication dated Dec. 1, 2014 in connection with European Patent Application No. 13740936.3, 6 pages.
GSN:AD057516, May 21, 2004, XP055151487, Retrieved from the internet: URL:http://ibis.internal.epo.org/exam/dbfetch.jsp?id=GSN:AD057516, 1 page.

(Continued)

*Primary Examiner* — Aaron Priest
(74) *Attorney, Agent, or Firm* — Amster, Rothstein & Ebenstein LLP (57) ABSTRACT

The present invention provides an oligonucleotide for HIV detection including a base sequence which is at least 80% identical to a base sequence composed of 10 or more continuous bases in a base sequence represented by SEQ ID NO. 1 or 6, and an HIV detection kit and an HIV detection method that uses the oligonucleotide for HIV detection.

2 Claims, 4 Drawing Sheets (56) References Cited

OTHER PUBLICATIONS

GSN:ADO57514, May 21, 2004, XP055151494, Retrieved from the internet: URL:http://ibis/exam/dbfetch.jsp?id+GSN:ADO57514, 1 page.
First Office Action dated Feb. 16, 2015 in connection with Chinese Patent Application No. 201380006301.9, 14, pages.
Bennasser Y et al., entitled "HIV-I encoded candidate mirco-RNAs and their cellular targets," Retrovirology 2004, I:43, 5 pages.

* cited by examiner

SEQUENCE LISTING

<160> NUMBER OF SEQ ID NOS: 6

<210> SEQ ID NO 1
<211> LENGTH: 65
<212> TYPE: DNA
<213> ORGANISM: Artificial Sequence
<220> FEATURE:
<223> OTHER INFORMATION: Target sequence based on HIV-1 TAR stem region

<400> SEQUENCE: 1

```
ggtctctctg gttagaccag atctgagcct gggagctctc tggctagcta gggaacccac    60
tgctt                                                                 65

<210> SEQ ID NO 2
<211> LENGTH: 24
<212> TYPE: DNA
<213> ORGANISM: Artificial Sequence
<220> FEATURE:
<223> OTHER INFORMATION: HIV-1 probe

<400> SEQUENCE: 2
ctagctagcc agagagctcc cagg                                            24

<210> SEQ ID NO 3
<211> LENGTH: 21
<212> TYPE: DNA
<213> ORGANISM: Artificial Sequence
<220> FEATURE:
<223> OTHER INFORMATION: HIV-1 primer

<400> SEQUENCE: 3
gggtctctct ggttagacca g                                               21

<210> SEQ ID NO 4
<211> LENGTH: 58
<212> TYPE: DNA
<213> ORGANISM: Artificial Sequence
<220> FEATURE:
<223> OTHER INFORMATION: Target sequence based on HIV-1 TAR stem region

<400> SEQUENCE: 4
ggtctctctg gttagaccag atctgagcct gggagctctc tggctagcta gggaaccc       58

<210> SEQ ID NO 5
<211> LENGTH: 22
<212> TYPE: DNA
<213> ORGANISM: Artificial Sequence
<220> FEATURE:
<223> OTHER INFORMATION: HIV-1 primer

<400> SEQUENCE: 5
ctggttagac cagatctgag cc                                              22

<210> SEQ ID NO 6
<211> LENGTH: 71
<212> TYPE: DNA
<213> ORGANISM: Artificial Sequence
<220> FEATURE:
<223> OTHER INFORMATION: Target sequence based on HIV-1 TAR stem region

<400> SEQUENCE: 6
ggtctctctg gttagaccag atctgagcct gggagctctc tggctagcta gggaacccac    60
tgcttaagcc t                                                          71
```

OLIGONUCLEOTIDE FOR HIV DETECTION, HIV DETECTION KIT, AND HIV DETECTION METHOD

CROSS-REFERENCE TO RELATED APPLICATIONS

This application is a U.S. national phase of PCT Application No. PCT/JP2013/051389, filed Jan. 24, 2013, which claims priority to Japanese Application No. JP 2012-013087, filed Jan. 25, 2012, the contents of which are incorporated by reference herein.

TECHNICAL FIELD

The present invention relates to an oligonucleotide for detecting a human immunodeficiency virus (hereinafter, referred to as HIV), an HIV detection kit, and an HIV detection method.

BACKGROUND ART

With respect to the HIV infection which is the cause of the acquired immune deficiency syndrome (hereinafter, referred to as AIDS), as well as taking fundamentally preventive measures against HIV infection, in case the suspicion for possible infection arises, it is important to establish a technique which is capable of early diagnosis of the presence or absence of infection.

Further, even when the HIV may seem to have disappeared from the body by treatment, if the detection sensitivity of the virus in diagnostic techniques is low, in spite of the HIV being latent in the body, there is a possibility of misdiagnosis that the HIV has "disappeared" from the body, leaving the root for AIDS recurrence.

In the acute infection period after the HIV infection, the HIV invades into a host cell, reverse transcribes its own viral RNA to synthesize DNA, inserts the DNA into the host cell DNA, and turns into a provirus. In a host cell, the provirus expresses the viral genes and packages the viral RNA with its own viral proteins, thereby forming the virus particles, and the virus particles are going outside the host cell.

Currently, as an anti-HIV therapeutic method in clinical trial, a therapy combining multiple drugs (Highly Active Anti-Retroviral Therapy: hereinafter, referred to as a HAART therapy) is common. The HAART therapy is a method of administering a several kinds of inhibitors that inhibit reverse transcription of the viral RNA, insertion of the viral DNA into the genomic DNA, and the like in the acute infection period as described above. By the HAART therapy, anti-HIV therapies have been achieved a remarkable development.

On the other hand, in the course of treatment with the HAART therapy, a portion of infected cells acquire resistance to the HAART therapy (hereinafter, these infected cells will be referred to as the latently infected cells). In the latently infected cells, in spite of having a provirus, the viral life cycle observed in the acute infection period is at rest, and the viral RNA is not produced. Since the HAART therapy is for inhibiting the steps of the viral replication as described above, elimination of the virus from the latently infected cells by the HAART therapy is difficult. However, if the HAART therapy is interrupted, the life cycle of the virus in the latently infected cells resumes.

Therefore, impossibility of virus removal from the latent infected cells is adversely affecting the quality of life (QOL) of HIV patients.

On the other hand, the inventors of the present invention have found that the latently infected cells produce a short RNA of about 60 bases when a model cell line was constructed and the phenotype of latently infected cells was analyzed by using the model cell lines (see Non-Patent Document 1).

In the method for diagnosing HIV infection, it is important to quantify the viral load in the blood of infected individuals as an index to determine the degree of the condition and the healing process.

Currently, an RNA quantitative method for HIV based on the real-time PCR method as the principle of amplification and detection of target nucleic acids is known as one of the rapid diagnostic methods of HIV infection.

As the RNA quantitative method for HIV using the real-time PCR method, for example, the method described in Patent Document 1 can be mentioned. The method described in Patent Document 1 is a method of amplifying and quantifying the HIV-1 provirus inserted into the genome using degenerate primers designed so as to recognize the various subtypes of HIV-1. Such a method is advantageous in that it can deal not only with the subtype B which is the main source of infection among Japanese infected individuals, but also with a variety of other subtypes.

CITATION LIST

Patent Document

[Patent Document 1] Japanese Unexamined Patent Application, First Publication No. 2007-295896

Non-Patent Document

[Non-Patent Document 1] Mizutani, et al., J Virol., Vol. 83, pages 11569-11580, 2009

SUMMARY OF INVENTION

Technical Problem

However, since HIV has a reverse transcriptase with a low fidelity (accuracy), it is a highly mutating virus. The oligonucleotide sequence described in Patent Document 1 which recognizes HIV is derived from a gag gene region encoding a structural protein GAG which is located approximately 500 bases downstream of the transcription start site, and it is insufficient to detect all the mutated viruses with high accuracy by using the sequence.

In addition, in an infected cell, it requires 12 days which is associated with the propagation of the virus from the infection exposure day until the viral RNA transcribed and extended which contains the GAG region becomes quantitatively detectable. For this reason, there is a demand for a technique which is capable of detecting viruses with high sensitivity at an earlier stage.

Further, even if the oligonucleotides described in Patent Document 1 is used, the short RNA produced by the latently infected cells described above cannot be detected, and there is still a room for improvement.

The present invention has been made in view of the above circumstances, and has an object of providing an oligonucleotide for HIV detection, an HIV detection kit and an HIV detection method which are capable of early detection of HIV with high accuracy and also high sensitivity.

Solution to Problem

In the present invention, as a result of intensive research aimed at achieving the above object, it has been found that a specific RNA is transcribed in HIV-infected cells in the latent infection period, and that a sequence which is unlikely to be mutated during reverse transcription is present in the viral RNA of the HIV, thereby completing the present invention.

The present invention provides an oligonucleotide for HIV detection, an HIV detection kit and an HIV detection method which have the following characteristics.

(1) An oligonucleotide for HIV detection, characterized by including a base sequence which is at least 80% identical to a base sequence composed of 10 or more continuous bases in a base sequence represented by SEQ ID NO. 1 or 6.

(2) The oligonucleotide for HIV detection according to (1), characterized by including a base sequence which is being at least 90% identical to a base sequence composed of 10 or more continuous bases in the base sequence represented by SEQ ID NO. 1 or 6.

(3) The oligonucleotide for HIV detection according to (1), characterized by including a base sequence which is being at least 95% identical to a base sequence composed of 10 or more continuous bases in the base sequence represented by SEQ ID NO. 1 or 6.

(4) The oligonucleotide for HIV detection according to (1), characterized by including a base sequence which is being at least 98% identical to a base sequence composed of 10 or more continuous bases in the base sequence represented by SEQ ID NO. 1 or 6.

(5) The oligonucleotide for HIV detection according to (1) including a base sequence composed of 10 or more continuous bases in the base sequence represented by SEQ ID NO. 1 or 6.

(6) An HIV detection kit characterized by including the oligonucleotide for HIV detection according to any one of (1) to (5).

(7) An HIV detection method characterized by using the oligonucleotide for HIV detection or the HIV detection kit according to any one of (1) to (6).

(8) An HIV detection method characterized by including: (a) a step of adding a polyA at the 3' end of an mRNA in a nucleic acid sample; (b) a step of synthesizing, from the mRNA, a cDNA complementary to the mRNA by a reverse transcription reaction using aan oligonucleotide having a polyT and a base sequence complementary to an adapter sequence on the 5' side of the polyT; (c) a step of amplifying, from the cDNA, a target base sequence having a sequence of a cDNA of HIV by using the oligonucleotide for HIV detection according to any one of (1) to (5) and an oligonucleotide having a base sequence complementary to the adapter sequence; and (d) a step of detecting an amplification product of the target base sequence.

Advantageous Effects of Invention

According to the present invention, in the HIV-infected cells, even if a mutation has occurred in HIV, such viruses can be detected with high accuracy.

In addition, according to the present invention, even in the latent infection period, HIV can be detected at an early stage with high sensitivity.

DESCRIPTION OF EMBODIMENTS

[Oligonucleotide for HIV Detection]

An oligonucleotide for HIV detection according to the present invention is at least 80% identical to a base sequence composed of 10 or more continuous bases in a base sequence represented by SEQ ID NO. 1 or 6. In the oligonucleotide for HIV detection of the present invention, within the scope of the identity, one or a plurality of bases may be deleted, inserted, or substituted for the base sequence represented by SEQ. ID. NO. 1 or 6.

Further, the oligonucleotide for HIV detection according to the present invention is preferably at least 90% identical, more preferably at least 95% identical, and particularly preferably at least 98% identical to a base sequence composed of 10 or more continuous bases in the base sequence represented by SEQ ID NO. 1 or 6. In addition, it is more preferable to include a base sequence composed of 10 or more continuous bases in the base sequence represented by SEQ ID NO. 1 or 6.

A base sequence represented by SEQ. ID. NO. 1 (5'-GGTCTCTCTGGTTAGACCAGATCTGAGC-CTGGGAGCTCTCTGGCTAGCTAGGG AACCCACT-GCTT-3': 65-mer) and a base sequence represented by SEQ. ID. NO. 6 (5'-GGTCTCTCTGGTTAGACCAGATCT-GAGCCTGGGAGCTCTCTGGCTAGCTAGGG AAC-CCACTGCTTAAGCCT-3': 71-mer) are a portion of the TAR (Trans Activation Responsive region) sequence present in the HIV LTR (Long Terminal Repeat) within the viral genome.

Two types of HIV, i.e., HIV-1 and HIV-2 can be mentioned as examples of HIV. The oligonucleotide for HIV detection according to the present invention can specifically detect only HIV-1 without depending on the subtype.

The TAR sequence of HIV is involved in the transcriptional control of viral genes, and is present in the LTR that is located at the 5' and 3' ends of the viral genome. The TAR sequence is highly conserved within the subtypes of HIV-1, and the transcription of viral genes is promoted by a transcriptional activator tat (Trans AcTivator) binding to the TAR sequence.

As described above, the TAR sequence is a site to which a transcriptional activator binds, and from the viewpoint that the transcription of viral genes is tightly regulated via the binding, the inventors of the present invention have discovered that the TAR sequence is a site unlikely to be mutated.

Therefore, since the oligonucleotide for HIV detection according to the present invention can also recognize the mutated HIV by including a sequence that recognizes the TAR sequence, it is possible to detect HIV with high accuracy.

The oligonucleotide for HIV detection according to the present invention is preferably a DNA, or may be one that includes an artificial nucleic acid, such as peptide nucleic acids (PNA) and locked nucleic acids (LNA), regardless of natural or non-natural, as long as it has the same functions as those of DNA.

The length of the oligonucleotide for HIV detection of the present invention is not particularly limited as long as it is the length required to function as a primer or a probe, but is preferably 10 to 40 bases long, and more preferably 20 to 30 bases long.

As described above, the inventors of the present invention have found that the latently infected cells produce a short RNA of about 60 bases when a model cell line was constructed and the phenotype of latently infected cells was analyzed by using the model cell lines.

Further, it has been revealed that the short RNA of about 60 bases is a complex of transcripts of the HIV-1 mRNA from the transcription initiation site to the nucleotide positions 50 to 70 at which the transcription stopped. In addition, it has also been revealed that the short RNA of about 60 bases is a complex of transcripts of the HIV-1 mRNA from the transcription initiation site to the nucleotide positions 50 to 71 at which the transcription stopped. That is, it has been revealed that the short RNA is one that corresponds to the mRNA starting from the nucleotide position 1 (transcription start site) of the TAR sequence present at the 5' end of the viral RNA, and ending at the nucleotide position from 50 to 70, or from 50 to 71.

Conventionally, the oligonucleotide sequence recognizing HIV has been derived from the gag gene region encoding the structural protein GAG which is located approximately 500 bases downstream of the transcription start site. Such oligonucleotides are not able to detect the short RNA produced by the latently infected cells. In addition, in an infected cell, it requires 12 days which is associated with the propagation of the virus from the infection exposure day until the viral RNA transcribed and extended which contains the GAG region becomes quantitatively detectable.

On the other hand, with regard to the life cycle of the virus in latently infected cells, although the level of virus production in serum is below the detection limit, the transcription is not completely stopped, and it is in a state where the transcription has been started, but the transcription and extension are not progressing efficiently. This situation is similar to that of the initial period of virus infection, and it is considered that the short RNA is also produced even in the initial period of virus infection. Therefore, according to the oligonucleotide for HIV detection of the present invention, it is possible to detect viruses at an early stage without waiting for 12 days from the infection exposure.

In addition, HIV-1 has the TAR sequence not only at the 5' end but also at the 3' end of the viral genome. Therefore, according to the oligonucleotide for HIV detection of the present invention, the virus can be detected with high sensitivity, since not only the detection of short RNA but also the detection of full length HIV-1 RNA is possible.

[HIV Detection Method]

First Embodiment

The HIV detection method of the present embodiment includes:

(a) a step of adding a polyA at the 3' end of an mRNA in a nucleic acid sample;

(b) a step of synthesizing, from the mRNA, a cDNA complementary to the mRNA by a reverse transcription reaction using an oligonucleotide having a polyT and a base sequence complementary to an adapter sequence on the 5' side of the polyT;

(c) a step of amplifying, from the cDNA, a target base sequence having a sequence of a cDNA of HIV by using the oligonucleotide for HIV detection of the present invention and an oligonucleotide having a base sequence complementary to the adapter sequence; and (d) a step of detecting an amplification product of the target base sequence.

Each of the steps will be described below.

First, in the step (a), a polyA is added at the 3' end of the mRNA in a nucleic acid sample.

The nucleic acid sample is not particularly limited as long as the sample contains a nucleic acid, but those obtained by extracting nucleic acids from samples including blood, lymph, cerebrospinal fluid and semen of the subjects, such as an infected individual who has been confirmed of HIV infection, an infection suspect who is suspected of HIV infection, and a patient undergoing an anti-HIV therapy, are preferred. Extraction of nucleic acids from these samples can be carried out by a conventional method, for example, by the use of Trizol, but in those cases where the detection target is a short RNA of about 60 bases as described above, it is preferable to employ a method of extracting low molecular RNAs such as micro-RNA.

As described above, the short RNA produced from the latently infected cells is one produced as a result of the transcription being stopped in the middle, and therefore does not have a polyA sequence at the 3' end thereof. In the present embodiment, by adding a polyA at the 3' end of the short RNA using a polyA polymerase, it is possible to make the short RNA to have a predetermined number of bases. As a result, it is possible to increase the efficiency of the reverse transcription reaction in step (b) and the amplification reaction of a target base sequence in step (c).

The length of the polyA is not particularly limited, but is preferably from 10 to 40 bases, and more preferably from 20 to 30 bases.

Then, in step (b), from the mRNA, a cDNA complementary to the mRNA is synthesized by a reverse transcription reaction using an oligonucleotide (hereinafter, also referred to as a polyT oligonucleotide) having a polyT and a base sequence complementary to an adapter sequence on the 5' side of the polyT.

The polyT of the polyT oligonucleotide anneals to the polyA added to the mRNA in step (a). The polyT oligonucleotides may have a degenerate sequence at the 3' end thereof and the cDNA complementary to the mRNA is synthesized in by a reverse transcription reaction in which the synthesis starts from the 3' end. As the reverse transcriptase used in the reverse transcription, those that are conventionally known are used, and, for example, the reverse transcriptase derived from Moloney Murine Leukemia Virus and the like can be mentioned.

The base sequence complementary to the adapter sequence possessed by the polyT oligonucleotide is not particularly limited as long as it does not inhibit the reverse transcription reaction, and those that are not complementary to known genes in vivo are preferred, and those that are not complementary to HIV genes are more preferred.

As with the length of the primers typically used, the length of the polyT oligonucleotide is preferably from 10 to 40 bases, and more preferably from 20 to 30 bases.

It should be noted that the step (a) and step (b) may be carried out simultaneously.

Further, since the cDNA synthesized by the reverse transcription reaction is hybridized with the mRNA used as a template, it is preferable to disassemble the mRNA in advance using an RNase such as RNaseH, prior to step (c).

Then, in step (c), from the cDNA, a target base sequence having a sequence of a cDNA of HIV is amplified by using the oligonucleotide for HIV detection of the present invention and an oligonucleotide having a base sequence complementary to the adapter sequence (hereinafter, also referred to as an adapter sequence recognizing oligonucleotide).

In the present invention, the aforementioned term target base sequence, more specifically, refers to those having a portion of the base sequence of cDNA of the TAR sequence.

As with the typical primers, the length of the adapter sequence recognizing oligonucleotide is preferably from 10 to 40 bases, and more preferably from 20 to 30 bases.

As a method for amplifying a target sequence, conventionally known methods such as PCR (Polymerase Chain Reaction), LAMP (Loop-Mediated Isothermal Amplification), NASBA (Nucleic Acid Sequence Based Amplification), ICAN (Isothermal and Chimerical primer-initiated Amplification of Nucleic acids), TRC (Transcription Reverse-Transcription Concerted), SDA (Strand Displacement Amplification), TMA (Transcription Mediated Amplification), SMAP (SMart Amplification Process), RPA (Recombines polymerase amplification), HDA (Helicase-dependent amplification), and the like can be mentioned.

DNA polymerase is a general term for an enzyme that synthesizes a DNA strand having a base sequence complementary to the template DNA to which the primer annealed.

The DNA polymerase used in the present invention is not particularly limited, but it is preferable to use a thermostable DNA polymerase such as a Taq DNA polymerase, a Tth DNA polymerase, and a Vent DNA polymerase, it is more preferable to use a DNA polymerase with a hot-start function in order to prevent extension before the test. In step (c), in the case of performing real-time PCR to be described later, it is particularly preferable to use a Taq DNA polymerase having 3'→5' exonuclease activity.

To take PCR as an example of a method for amplifying a target base sequence, the oligonucleotide for HIV detection of the present invention is annealed to the 3' end of the cDNA synthesized in step (b), followed by the extension reaction, and a complementary strand of the cDNA (hereinafter, referred to as an extension product A) is synthesized.

Subsequently, the adapter sequence recognizing oligonucleotide is annealed to the 3' end of the extension product A, followed by the extension reaction, and a complementary strand of the extension product A (hereinafter, referred to as an extension product B) is synthesized.

Then, the oligonucleotide for HIV detection of the present invention is annealed to the 3' end of the extension product B, followed by the extension reaction, and a complementary strand of the extension product B (hereinafter referred to as an extension product C) is synthesized.

After that, by repeating the step of synthesizing the extension product B and the step of synthesizing the extension product C, the target base sequence is amplified.

Note that for the setting of the amplification program such as the temperature in the PCR, it is possible to carry this out by a conventional method.

The reaction conditions for the oligonucleotide for HIV detection of the present invention or the adapter sequence recognizing oligonucleotide to anneal to the target base sequence are not particularly limited, and can be set under the typical conditions, such as the temperature, pH, salt concentration and buffer solution, in consideration of the Tm value and the like of each oligonucleotide.

In the present embodiment, a primer set composed of the oligonucleotide for HIV detection of the present invention and the adapter sequence recognizing oligonucleotide is used. As mentioned above, the oligonucleotide for HIV detection of the present invention recognizes the site that is unlikely to be subjected to mutation. Further, since the aforementioned primer set has only one HIV recognition site, it is less likely to be affected by mutation of the viral RNA.

Therefore, according to the present embodiment, it is possible to detect all the mutated viruses with high accuracy.

Then, in step (d), the amplification product of the target base sequence is detected.

Examples of typical detection methods in step (d) include an end-point assay to evaluate whether the target base sequence has been amplified or not after the reaction, and a real-time assay to measure the amplification of the target base sequence over time (real-time).

As the end-point assay, a method of evaluating the amplification of a target base sequence by electrophoresis can be mentioned. The method is a method to evaluate whether a target base sequence having a predetermined molecular weight is amplified or not by subjecting the amplification products of the target base sequence and a nucleic acid molecular weight marker to electrophoresis, and comparing the mobility of the two.

As the reagent used in the detection by electrophoresis, ethidium bromide or SYBR Green that fluoresces by binding to double-stranded DNA is preferred.

As the real-time assay, an evaluation method using a real-time PCR machine can be mentioned. Real time PCR is a method, by using a known amount of DNA which has been serially diluted as a standard, for measuring amplification of the standard DNA and the target base sequence by PCR over time, and quantifying the number of molecules of the target base sequence present in the nucleic acid sample, within the range of the number of molecules in which the amplification of standard DNA occurs exponentially.

Real-time PCR is excellent in that it is capable of elucidating not only the presence or absence of HIV infection, but also the degree of the condition and the healing process by quantifying the viral load in the blood of patients with HIV or HIV-infected individuals.

As the quantitative method in real-time PCR, a method using a fluorescent dye can be mentioned, and specific examples thereof include a method using a dye, such as SYBR Green, that specifically intercalates into double-stranded DNA and emits fluorescence, and a method using a probe prepared by binding a fluorescent dye to an oligonucleotide specific to the DNA to be amplified. From the viewpoint of detecting the amplification of the target base sequence more specifically, the latter method is preferred.

The probe used in the latter method is one having both ends of oligonucleotide, capable of hybridizing to a portion of the target base sequence, modified with a fluorescent substance and a quencher, respectively. In such a probe, since the fluorescent substance and the quencher are in close proximity, the function of the fluorescent substance to generate a fluorescent signal has been hampered by the quencher.

In the aforementioned step (c), the probe hybridizes to a target base sequence under the conditions in which the oligonucleotide for HIV detection of the present invention anneals to the target base sequence. Subsequently, in the course of the extension reaction, the probe is broken down by the 5'→3' exonuclease activity of the Taq DNA polymerase. As a result, the fluorescent substance and the quencher being modified in the probe are spatially separated from each other, and the fluorescent substance can emit a fluorescent signal. Such a fluorescent signal is proportional to the number of molecules of the target base sequence which has been amplified.

Examples of the fluorescent substance include FAM™ (carboxyfluorescein), JOE™ (6-carboxy-4',5'-dichloro-2',7'-dimethoxyfluorescein), FITC™ (fluorescein isothiocyanate), TET™ (tetrachlorofluorescein), HEX™ (5'-hexachloro-fluorescein-CE phosphoramidite), Cy3, Cy5, and Alexa568.

Further, as the quencher, TAMRA™ (tetramethyl-rhodamine), 4-(4-dimethylaminophenylazo)benzoic acid (DABCYL™), BHQ™ and the like can be mentioned.

The base sequence of the oligonucleotides to be used as a probe is not particularly limited as long as it is capable of recognizing the TAR sequence or capable of hybridizing to a sequence complementary to the TAR sequence, and preferred examples of the base sequence include a base sequence represented by SEQ. ID. NO. 2 (5'-CTAGCTAGC-CAGAGAGCTCCCAGG-3': 24mer).

By using such probes, it is possible to detect more specifically the amplification of the target base sequence.

As the other detection method in step (d) is not particularly limited, and examples thereof include labeling of oligonucleotides with a fluorescent dye or the like, high performance liquid chromatography, mass spectrometry, melting curve analysis, growth curve analysis, and the like.

For the labeling of oligonucleotides with a fluorescent dye or the like, for example, a method of labeling the oligonucleotide for HIV detection or the adapter sequence recognizing oligonucleotide with a labeling substance can be employed. By employing such a method, it is possible to detect the amplification of a target base sequence using the labeling substance as an indicator. As the labeling substance, for example, fluorescent dyes, energy absorbing materials, radioisotopes, chemiluminescent bodies, enzymes, antibodies and the like can be mentioned. The position of the oligonucleotide to be labeled with such a labeling substance is not particularly limited, and the positions that do not inhibit the extension reaction are preferred.

The HIV detection method of the present embodiment has a step (a) of adding a polyA at the 3' end of the HIV-derived mRNA in a nucleic acid sample, but may not have a step (a) in the case of targeting the entire length of HIV RNA for detection, because polyA is already added to the 3' end thereof.

Further, in the case of targeting the entire length of HIV RNA for detection, in step (c), in place of the adapter sequence recognizing oligonucleotide, an oligonucleotide having a base sequence complementary to the base sequence derived from HIV or an oligonucleotide capable of hybridizing to the base sequence derived from HIV may be used.

In this case, in view of the amplification efficiency, it is preferable that the oligonucleotide for HIV detection of the present invention recognize the TAR sequence located at the 3' end of the viral genome.

[HIV Detection Kit]

The HIV detection kit of the present invention includes the oligonucleotide for HIV detection of the present invention described above. In addition, the HIV detection kit of the present invention may include a cell disruption reagent for the pre-treatment of nucleic acid samples and the reagents that are explained in each step of the HIV detection method of the present invention described above.

As described above, by combining the reagents necessary for the HIV detection method of the present invention as a kit, it is possible to detect HIV more easily and also in a short period of time.

As described above, in the present invention, it has been found that a sequence which is unlikely to be mutated during reverse transcription is present in the viral RNA of HIV. By using such sequences for the HIV diagnosis, even if mutations have occurred in the HIV in HIV-infected cells, it is possible to detect the HIV with high accuracy.

Further, in the present invention, it has been observed that specific RNA is transcribed in HIV-infected cells in the latent infection period, and a method of detecting the initial transcript expressed by HIV has been established. As a result, it is possible to reduce the number of days required for the HIV detection, enable detection with high sensitivity, and contribute to the early diagnosis of HIV infection. In addition, by the early diagnosis, it is possible to delay the time for disease onset and the initiation of therapy with respect to AIDS.

In the present invention, it is possible to determine the reactivation of virus at an early stage from the body of the patient in treatment of AIDS under the administration of antiviral drugs.

In addition, it is also possible to apply the principle of HIV detection method of the present invention to the detection of other viruses and the like that are known to establish latent infection.

EXAMPLES

A more detailed description of the present invention is presented below by showing the following examples, but the present invention is not limited to the following examples.

Experimental Example 1

Detection of Short RNA

Figure 5:
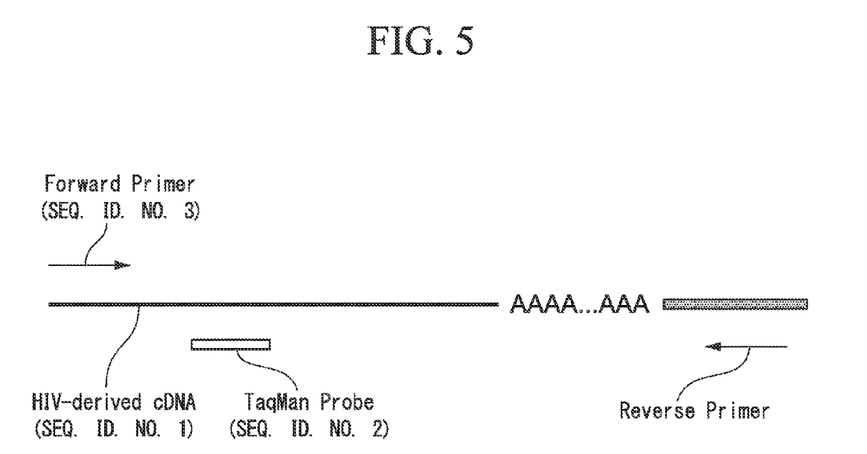
FIG. 5 is an explanatory view of the detection system of the short RNA produced in the HIV-infected cells, according to the present invention.

A system for detecting the short RNA produced in the HIV-infected cells was established using quantitative PCR (FIG. 5). As a quantitative PCR reagent, the premix Extaq™ kit (manufactured by Takara Bio Inc.) was used.

An oligonucleotide represented by the SEQ ID NO: 3 (5'-GGGTCTCTCTGGTTAGACCAG-3': 21-mer) was used as a Forward Primer, and an adapter sequence recognizing oligonucleotide attached to the miScript Primer Assay Kit was used as a Reverse Primer. An oligonucleotide shown by the SEQ ID NO: 2 (5'-CTAGCTAGCCAGAGAGCTC-CCAGG-3': 24-mer) which was modified with FAM™ at the 5' end and with TAMRA™ at the 3' end was used as the Taqman™ Probe. The synthesis of these oligonucleotides was commissioned to a commercial oligo house.

10 µl of a mixed solution composed of the quantitative PCR reagent described above, the oligonucleotides described above, and 75 ng of cDNA per well was dispensed into each well of a 96 well plate.

As a quantitative PCR machine, the ABI7300 (manufactured by Life Technologies Corporation) was used, and 40 cycles consisting of a reaction at 95° C. for 30 seconds, followed by a two-step reaction at 95° C. for 5 seconds and 60° C. for 34 seconds were carried out.

Quantitative PCR was performed using GAPDH™ as the standard DNA to prepare a standard curve.

Example 1

According to the method described in J Virol., Vol. 83, pages 11569-11580, 2009, a vector expressing transcripts obtained by the transcription starting from the transcription start site of the RNA of HIV-1 and ending at the uracil at position 61 was introduced into the U1 cell line, the model cells of the latently infected cells of HIV-1, which is published in J Virol., Vol. 72, pages 1666-1670, 1998, thereby producing a stable cell line U1-mU6-TAR. Total RNA was extracted from the cells using the mirVana™ microRNA isolation kit (manufactured by Ambion Inc.), and cDNA was synthesized from the short RNA in Total RNA using the miScript Primer Assay Kit (manufactured by Qiagen™).

Quantitative PCR was performed by using the cDNA, the number of copies of the target base sequence in the stable cell line U1-mU6-TAR was determined.

Example 2 cDNA was synthesized in the same manner as in Example 1 from the U1 cell line carrying a wild-type HIV-1 as the model cells of latently infected cells which has been published in J Virol., Vol. 72, pages 1666-1670, 1998, and the number of copies of the target base sequence in the U1 cell line was determined.

Comparative Example 1

Quantitative PCR was performed in the same manner as in Example 1 with the exception that sterile water was used in place of the cDNA solution.

Figure 1:
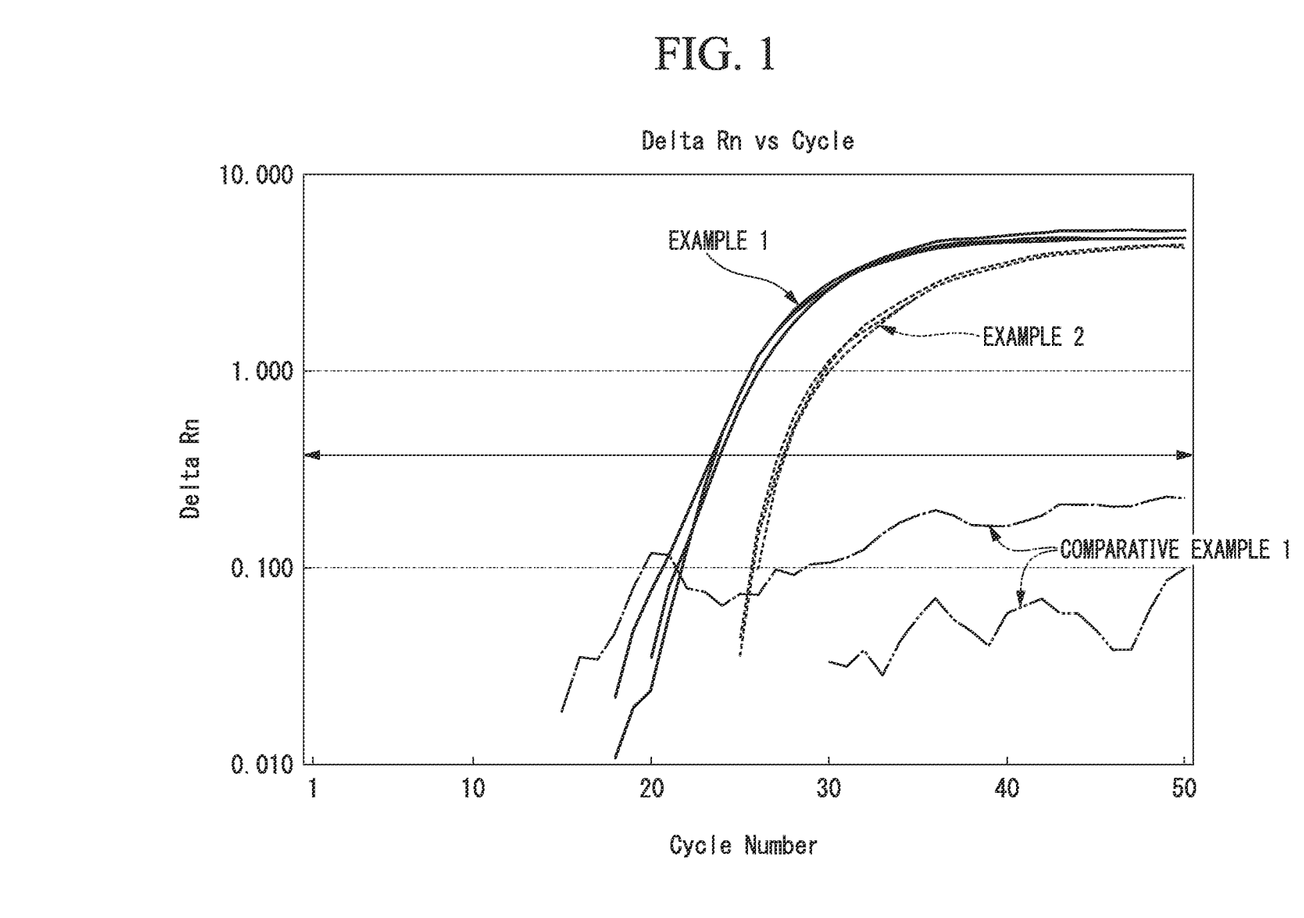
FIG. 1 are results of the detection of HIV-1 short RNA using Real Time PCR in Example 1, Example 2, and Comparative Example 1.

The measurement results using the quantitative PCR machine in Examples 1 and 2 and Comparative Example 1 are shown in FIG. 1. As shown in FIG. 1, it was confirmed that in the reactions in Examples 1 and 2, the signal was enhanced as the number of cycles increased. On the other hand, in Comparative Example 1 where the cDNA was absent in the reaction system, the enhancement of signal was not confirmed even when the number of cycles was increased.

From the calculation results using a standard curve, in the stable cell line U1-mU6-TAR used in Example 1, as compared with the latently infected cell line U1 which was used in Example 2, approximately 8-fold copies of short transcripts were confirmed.

As described above, from the results of Examples 1 and 2, according to the present invention, it was confirmed that the short RNA produced in the infected cells could be quantified. From these results, it was discovered that it was possible to detect HIV early at an initial stage of the infection.

Experimental Example 2

Identification of Short RNA

Deep Sequence analysis by Illumina GAIIx (manufactured by Illumina Inc.™) was performed using the PCR product of Example 2 to analyze the base sequence of the short RNA of about 60 bases. The results are shown in FIG. 2.

Figure 2:
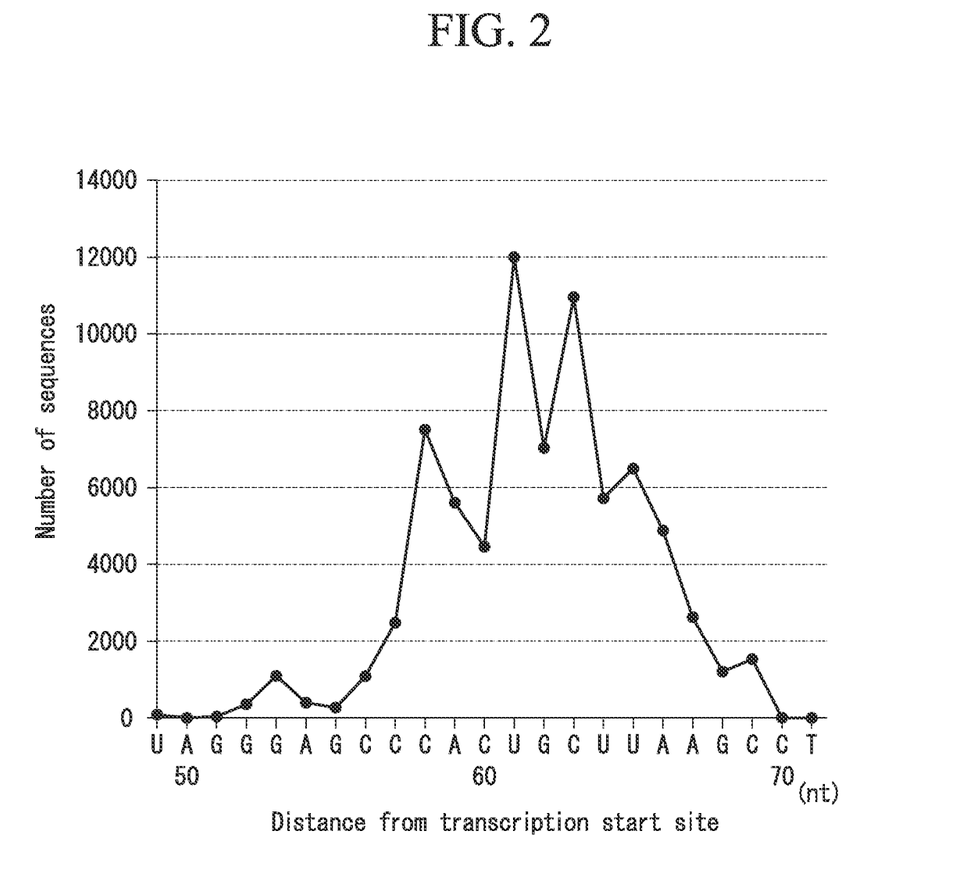
FIG. 2 is an analysis result of a base sequence of a short RNA of about 60 bases in Experimental Example 2.

As shown in FIG. 2, it became apparent that the short RNAs of about 60 bases were transcripts from the transcription start site of the RNA of HIV-1 to the nucleotide position 50 to 70 at which the transcription stopped. Further, it also became clear that the short RNAs of about 60 bases were transcripts from the transcription start site of the RNA of HIV-1 to the nucleotide position 50 to 71 at which the transcription stopped.

Experimental Example 3

Determination of the Copy Number of Short RNA

Using an oligonucleotide synthesized in vitro and represented by SEQ ID NO 4 (5'-GGTCTCTCTGGTTAGAC-CAGATCTGAGCCTGGGAGCTCTCTG-GCTAGCTAGGGAACCC-3': 58-mer) as a standard RNA, a dilution series of cDNA, which was a 10-fold dilution from $10^8$ copies to 10 copies, was prepared in the same manner as in Example 1, followed by quantitative PCR as described below, to produce a calibration curve.

An oligonucleotide represented by the SEQ ID NO. 5 (5'-CTGGTTAGACCAGATCTGAGCC-3': 22-mer) was used as a Forward Primer, and an adapter sequence recognizing oligonucleotide attached to the miScript Primer Assay Kit was used as a Reverse Primer. An oligonucleotide shown by the SEQ ID NO. 2 (5'-CTAGCTAGCCAGAGAGCTC-CCAGG-3': 24-mer) which was modified with FAM™ at the 5' end and with BHQ-1 at the 3' end was used as the Taqman™ Probe. The synthesis of these oligonucleotides was commissioned to a commercial oligo house.

20 µl of a mixed solution composed of the quantitative PCR reagent described above, the oligonucleotides described above, and 75 ng of cDNA per well was dispensed into each well of a 96 well plate.

As a quantitative PCR machine, the CFX-96 (manufactured by Bio-Rad Laboratories, Inc.) was used, and 50 cycles consisting of a reaction at 95° C. for 30 seconds, followed by a two-step reaction at 95° C. for 5 seconds and at 60° C. for 10 seconds were carried out.

Figure 3:
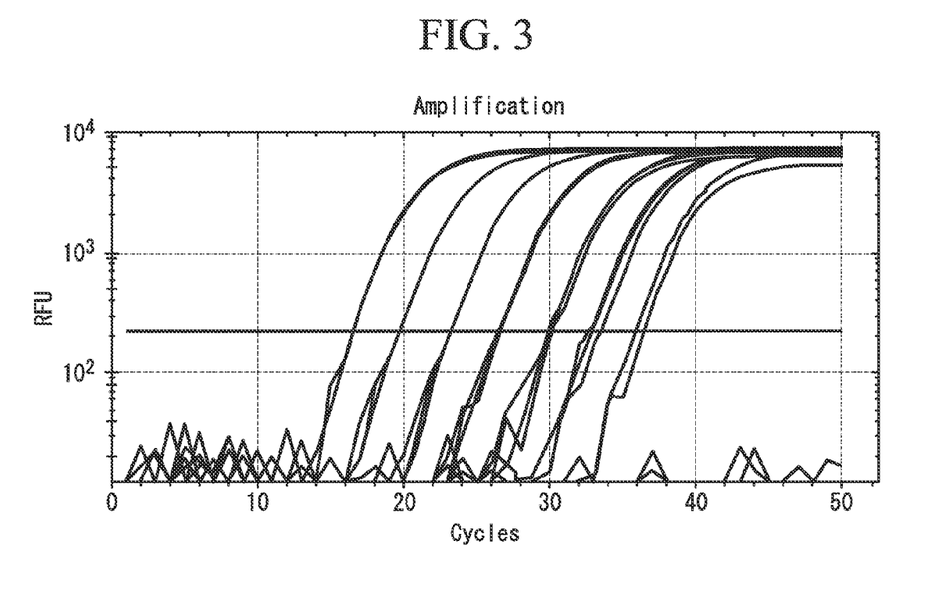
FIG. 3 is the result of quantitative PCR in Experimental Example 3.
Figure 4:
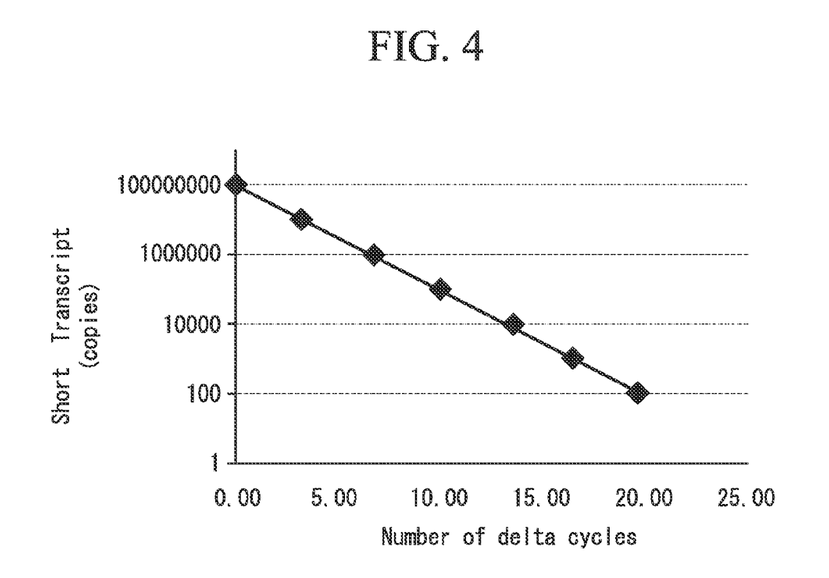
FIG. 4 is a calibration curve in Experimental Example 3.

The results of the quantitative PCR are shown in FIG. 3, and the calibration curve is shown in FIG. 4. It is possible to detect a signal quantitatively from the RNA of $10^8$ copies to 100 copies.

From the above results, according to the present invention, it is apparent that it is possible to detect HIV at an early stage with high accuracy and also high sensitivity.

INDUSTRIAL APPLICABILITY

According to the present invention, in the HIV-infected cells, even if a mutation has occurred in HIV, such viruses can be detected with high accuracy, and even in the latent infection period, HIV can be detected at an early stage with high sensitivity, and therefore it is industrially useful.

The invention claimed is:

1. An HIV detection kit comprising
   a polyA polymerase;
   an oligonucleotide having a polyT and a base sequence complementary to an adapter sequence on the 5' side of the polyT, wherein the base sequence complementary to the adapter sequence is not complementary to an HIV gene;
   a primer set for HIV detection which consists of a forward primer and a reverse primer, wherein the forward primer comprises SEQ ID NO: 5 and the reverse primer consists of the base sequence complementary to the adapter sequence; and
   a probe having the base sequence comprising SEQ ID NO: 2, wherein the probe is labelled with a fluorescent dye, a radioisotope, a chemiluminescent body, an enzyme, or an antibody.

2. A method of detecting an HIV by detecting a short RNA produced by HIV-infected cells, wherein the short RNA produced by HIV-infected cells is a complex of transcripts of the HIV-1 mRNA from the transcription initiation site to the nucleotide position 50 to 71 of SEQ ID NO: 1 at which the transcription stops, which method comprises using the HIV detection kit of claim 1 for:

(a) adding a polyA at the 3' end of the short RNA produced by HIV-infected cells in a nucleic acid sample using the polyA polymerase;

(b) synthesizing, from the mRNA, a cDNA complementary to the mRNA by a reverse transcription reaction using the oligonucleotide having a polyT and a base sequence complementary to an adapter sequence on the 5' side of the polyT, wherein the base sequence complementary to the adapter sequence is not complementary to an HIV gene;

(c) amplifying, from the cDNA, a target base sequence having a sequence of a cDNA of HIV by using the primer set for HIV detection of the HIV detection kit wherein the primer set comprises the forward primer comprising SEQ ID NO: 5 and the reverse primer having a base sequence complementary to the adapter sequence; and (d) detecting an amplification product of the target base sequence using the probe having the base sequence comprising SEQ ID NO: 2 wherein the probe is labelled with a fluorescent dye, a radioisotope, a chemiluminescent body, an enzyme, or an antibody, thereby detecting the HIV.

\* \* \* \* \*